United States Patent [19]
Harris

[11] 3,957,046
[45] May 18, 1976

[54] DISPOSABLE MOUTH TO MOUTH RESUSCITATION DEVICE

[75] Inventor: Arthur M. Harris, Miami Shores, Fla.

[73] Assignee: Salvatore G. Militana, Miami Shores, Fla.

[22] Filed: Nov. 27, 1974

[21] Appl. No.: 527,883

[52] U.S. Cl. ............................................ 128/145.5
[51] Int. Cl.² ........................................... A62B 7/00
[58] Field of Search............ 128/145.5, 145.6, 145.7, 128/147, 146.4, 146.5, 140 R, 141 R, 202, 211, 274, 185

[56] References Cited
UNITED STATES PATENTS

| | | | |
|---|---|---|---|
| 48,789 | 7/1865 | Bullock | 128/211 |
| 2,887,105 | 5/1959 | Brown et al. | 128/145.5 |
| 3,124,124 | 3/1964 | Cross | 128/145.5 |
| 3,242,921 | 3/1966 | Seeler | 128/145.5 |
| 3,395,700 | 8/1968 | Stillman | 128/145.5 |
| 3,518,989 | 7/1970 | Seeler | 128/145.5 |

*Primary Examiner*—Robert W. Michell
*Assistant Examiner*—Henry J. Recla
*Attorney, Agent, or Firm*—Salvatore G. Militana

[57] ABSTRACT

A disposable mouth to mouth resuscitation device consisting of a pair of tubular members cemented together in end to end relation with a pair of valve discs in contact with each other interposed therebetween; one of the valve discs being rigid and the other flexible. Upon the person performing the resuscitation breathes into the tubular member having the rigid valve disc adjacent thereto, the flexible valve disc is made to flex away from the rigid valve disc and permit the air to pass through the second tubular member and into the person's mouth being resuscitated. Each exhalation of air and any vomit emitted by the person being resuscitated cause the flexible valve disc to seal against the rigid valve disc and be discharged to the atmosphere through openings formed in the side of the second tubular member. When the person performing the resuscitation breathes into the first tubular member, he closes off the openings with his fingers as well as the nostrils of the person being resuscitated and removes them when the latter exhales.

2 Claims, 6 Drawing Figures

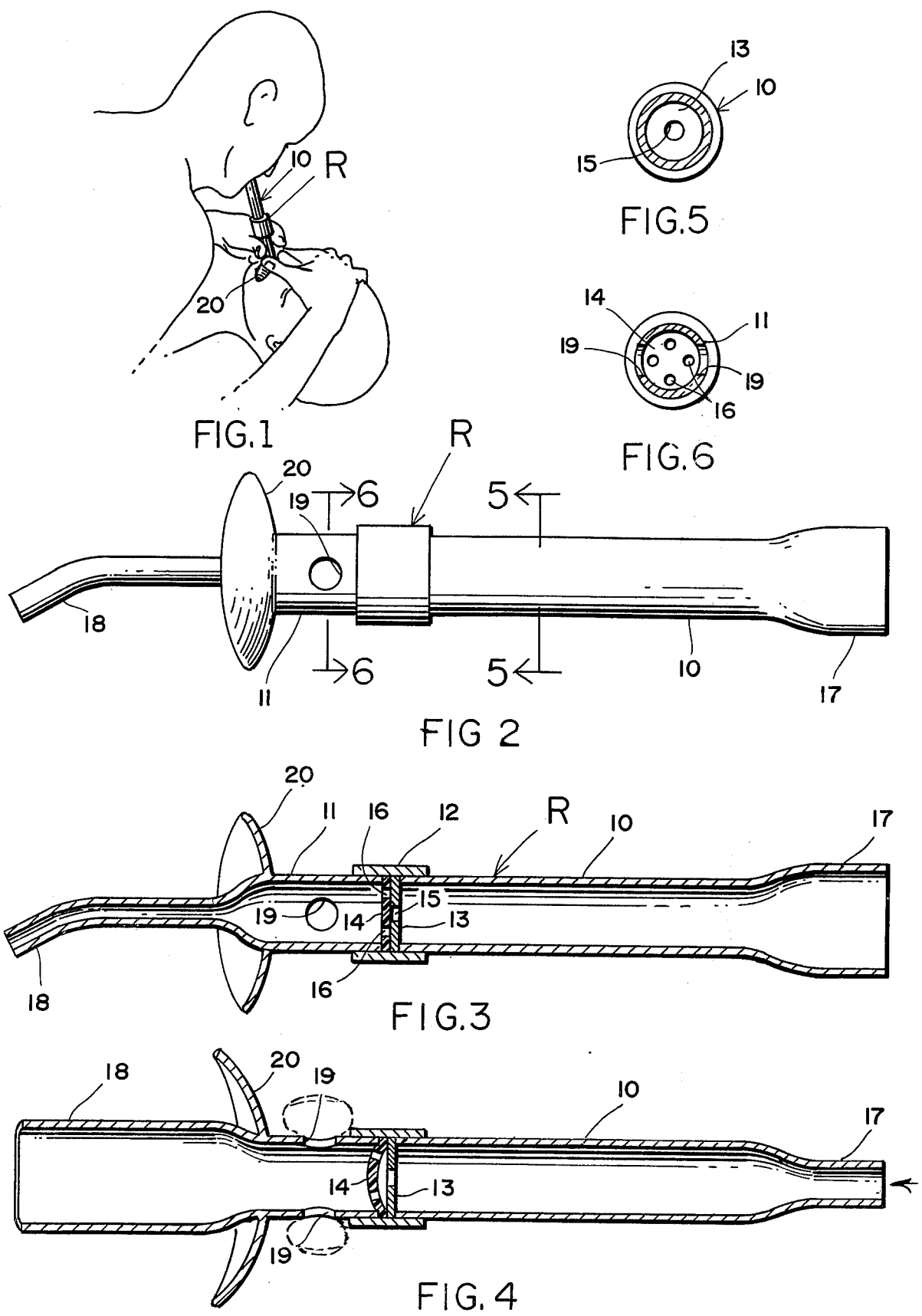

DISPOSABLE MOUTH TO MOUTH RESUSCITATION DEVICE

BACKGROUND OF THE INVENTION

1. Field of the Invention

This invention relates to mouth to mouth resuscitation devices and is more particularly directed to one which is of such simple construction, it can be disposed of after being used.

2. Description of the Prior Art

The conventional mouth to mouth resuscitation devices must be sterilized after each use since the cost thereof is prohibitive to permit the disposing of the device after use. These devices are complicated in construction and design and consequently are too costly to consider using them only once. All resuscitation devices have valve structures that must permit the air being breathed into the victim's mouth to pass readily therethrough yet prevent the air or vomit exhaled by the victim to contact the person performing the resuscitation. Consequently after each use of these devices, they must be cleaned and sterilized so that there is no danger of contaminating the next user of the device. The present invention contemplates avoiding the above indicated objection by providing a resuscitation device that is so simple in design and construction and inexpensive in cost as to render it disposable after a single use thereof.

SUMMARY OF THE INVENTION

Therefore, a principal object of the present invention is to provide a mouth to mouth resuscitation device that is simple in construction and design, consisting of a minimum of parts and of such low cost that the device may be used only once and disposed rather than having to sterilize it to permit reuse thereof.

Another object of the present invention is to provide a mouth to mouth resuscitation device having a pair of tubular members joined together end to end with a pair of valves therebetween to permit the flow of breathed air to the victim or person being resuscitated but not permitting any exhaled air or vomit from the victim coming into contact with the other person.

A further object of the present invention is to provide a mouth to mouth resuscitation device having a rigid valve and a flexible valve which operate together to permit the flow of fluid only in one direction.

With these and other objects in view, the invention will be best understood from a consideration of the following detailed description taken in connection with the accompanying drawing forming a part of this specification, with the understanding, however, that the invention is not confined to any strict conformity with the showing of the drawing but may be changed or modified so long as such changes or modifications mark no material departure from the salient features of the invention as expressed in the appended claims.

BRIEF DESCRIPTION OF THE DRAWING

In the drawing:

FIG. 1 is a perspective view of a person being resuscitated by a second person utilizing my disposable resuscitation device.

FIG. 2 is a side plan view of my device.

FIG. 3 is a cross sectional view taken through a plane passing through the centerline of the device.

FIG. 4 is a similar view taken through a plane at 90° from that of FIG. 3 showing the action of the flexible valve when air is passing therethrough.

FIGS. 5 and 6 are cross sectional view taken along the lines 5—5 and 6—6 of FIG. 2.

DESCRIPTION OF THE PREFERRED EMBODIMENT

Referring to the drawing wherein like numerals and letter are used to designate similar parts throughout the several views, the letter —R— refers to my disposable mouth to mouth resuscitation device consisting of a pair of tubular members 10 and 11 mounted in axial alignment with each other and joined together by a sleeve 12 that is cemented to and overlapping the inner ends of the tubular members 10 and 11. Between the inner ends of the tubular members 10 and 11 is a pair of valve members 13 and 14 that are engaged by direction ends of the tubular members 10 and 11 and in side by side contact relation as best shown by FIG. 3. The valve 13 which is rigid in structure is provided with a centrally disposed opening 15. The valve 14 is constructed of flexible material and is provided with a plurality of openings 16 which are out of alignment with the opening 15 of the rigid valve 13. It is obvious that when the valve discs 13 and 14 are in contact with each other as shown by FIG. 3, the flow of fluid is permitted only in one directio therethrough, as is explained in detail hereinafter.

As in conventional resuscitation devices, the tubular member 10 is tapered as at 17 to permit the person performing the resuscitation to place his lips thereon and breathe into the tubular member 10.

The tubular member 11 has its free end likewise tapered as at 18 but also bent at a slight angle, as best shown by FIGS. 2 and 3 to permit the person performing the resuscitation to place the end portion 18 on the tongue of the victim to prevent the latter from swallowing his tongue and at the same time place the discharge end 18 in proximity of the victims throat passage without causing gagging effect. The tubular member 11 is provided with a pair of oppositely positioned openings 19 and a breathing mask 20. The function of the breathing mask 20 is to close off the entire mouth of the victim to comepl the air being breathed into his mouth to flow into his lungs and not escape at the sides of the mouth which has to be in an open position to receive the tubular member 11.

In the normal use of my device -R- the victims mouth is opened and the curved end 18 of the tubular member 11 is placed on his tongue and slid inwardly until the breathing mask 20 engages the victim's face. The person performing the resuscitation then places a thumb and a finger shown by dotted lines in FIG. 4 of one hand over the openings 19 and the thumb and finger of the other hand to close off the victim's nostrils. Then he breathes into the mouth piece 17 in accordance with the normal proceedures for the resuscitation of persons. Between each breath he releases his thumbs and fingers from the openings 19 and the victim's nostrils to permit the victim to exhale.

When the person performing the resuscitation breathes into the mouthpiece 17, the air pressure in the tubular member 10 will cause the flexible valve disc 14 to flex away from the rigid valve disc 13 to permit the air to flow through the valve openings 13 and 16. With the openings 19 closed off the air must flow into the victim's lungs. When the victim exhales, the pressure of the air or any fluids that might be expelled by the victim will cause the flexible valve disc 14 to flex back to contact relation with the rigid valve disc 13, and thereby prevent any flow of fluid or air therethrough. Since the user's fingers and thumbs have been removed from the openings 19 and the victim's notstrils, the expelled air and fluid will be discharged therethrough without contacting the person performing the resuscitation.

Since each of the parts, namely, the tubular members 10 and 11, sleeve 12 and the valve discs 13 and 14 can be molded of plastic material and since the assembly of the device —R— is obviously very simple, the cost of my resuscitation device —R— is minimal and can be economically disposed after a single use, rather than having to sterilize the device. To properly sterilize such a device will require the disassembly of the device before boiling same, in order that all contaminating matter that may be trapped therein is eliminated.

What I claim as new and desire to secure by Letters Patent is:

1. A mouth to mouth resuscitating device comprising first and second tubular members in substantially coaxial relation and having first and second end portions respectively, a substantially rigid valve member and a flexible valve member mounted between said second end portions of said respective tubular members in substantially complete contact relation with each other, said second end portions of said respective tubular members engaging and securing said valve members at their periphery, a sleeve member telescopically mounted on both of said tubular members and engaging said tubular members along its full length at said second end portions of each respective tubular member thereby securing said tubular members together, said rigid valve member having a centrally disposed opening and disposed transversely adjacent the second end portion of said second tubular member, said flexible valve member having openings out of alignment with said centrally disposed opening and disposed transversely adjacent the second end portion of said first tubular member, the first end portion of each of said tubular members being tapered for insertion into the mouths of persons using this device, the first end portion of said first tubular member being arcuate to extend over and engage the tongue of the person being resuscitated, said first tubular member having an opening in its side wall adjacent said flexible valve member whereby upon the person performing the resuscitation breathes into the other of said tubular member, said flexible valve member is compelled to flex away from said rigid valve member and upon simultaneously closing off said opening, said air is compelled to flow through said first tubular member and into said person being resuscitated.

2. The structure as recited by amended claim 1 taken in combination with an arcuate face mask extending about the periphery of said first tubular member between said free end of said first tubular member and said opening.

* * * * *